United States Patent
Bauman et al.

(10) Patent No.: US 8,859,290 B2
(45) Date of Patent: Oct. 14, 2014

(54) INHIBITORS OF INFLUENZA ENDONUCLEASE ACTIVITY AND TOOLS FOR THEIR DISCOVERY

(75) Inventors: Joseph D. Bauman, New Brunswick, NJ (US); Kalyan Das, New Brunswick, NJ (US); Disha Patel, New Brunswick, NJ (US); Eddy Arnold, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/554,709

(22) Filed: Jul. 20, 2012

(65) Prior Publication Data

US 2013/0090300 A1  Apr. 11, 2013

Related U.S. Application Data

(60) Provisional application No. 61/510,731, filed on Jul. 22, 2011.

(51) Int. Cl.
| | | |
|---|---|---|
| C07K 14/11 | (2006.01) |
| G01N 33/00 | (2006.01) |
| C12N 9/22 | (2006.01) |
| A61K 31/352 | (2006.01) |
| A61K 31/7076 | (2006.01) |
| C12N 9/16 | (2006.01) |
| A61K 31/404 | (2006.01) |
| C12Q 1/34 | (2006.01) |
| A61K 31/121 | (2006.01) |
| A61K 31/402 | (2006.01) |
| A61K 31/353 | (2006.01) |
| A61K 31/472 | (2006.01) |

(52) U.S. Cl.
CPC ............ *A61K 31/7076* (2013.01); *C12N 9/22* (2013.01); *A61K 31/352* (2013.01); *C12N 9/16* (2013.01); *C07K 2299/00* (2013.01); *A61K 31/404* (2013.01); *C12Q 1/34* (2013.01); *A61K 31/121* (2013.01); *A61K 31/402* (2013.01); *G01N 2500/02* (2013.01); *A61K 31/353* (2013.01); *A61K 31/472* (2013.01)
USPC .............................. 436/86; 530/350; 530/418

(58) Field of Classification Search
None
See application file for complete search history.

(56) References Cited

U.S. PATENT DOCUMENTS

2013/0023565 A1*  1/2013  Cusack et al. ................. 514/330

FOREIGN PATENT DOCUMENTS

WO    WO 2010/069600    *   6/2010

OTHER PUBLICATIONS

Saleem et al. Appl. Microbiol. Biotechnol. 2007, 75, 1385-1392.*
Wiencek, J. M. Ann. Rev. Biomed. Eng. 1999, 1, 505-534.*
GE Healthcare Data file 28-9622-84 AA "GST Fusion System" Dec. 2009.*
Bloom et al., "Permissive secondary mutations enable the evolution of influenza oseltamivir resistance", *Science 328*, 1272-1275, (2010).
Congreve et al., "Recent developments in fragment-based drug discovery", *J Med Chem.*, 51(13), 3661-3680, (2008).
Das et al., "Structures of influenza A proteins and insights into antiviral drug targets", *Nat Struct Mol Biol.*, 17(5), 530-538, (2010).

(Continued)

*Primary Examiner* — Nashaat Nashed
(74) *Attorney, Agent, or Firm* — Viksnins Harris & Padys PLLP

(57) ABSTRACT

The invention provides inhibitors of influenza endonuclease activity and tools for their discovery.

14 Claims, 8 Drawing Sheets

(56) References Cited

OTHER PUBLICATIONS

Dias et al., "The cap-snatching endonuclease of influenza virus polymerase resides in the PA subunit", *Nature* 458, 914-918, (2009).

Hara et al., "Amino acid residues in the N-terminal region of the PA subunit of influenza A virus RNA polymerase play a critical role in protein stability, endonuclease activity, cap binding, and virion RNA promoter binding", *J Virol.*, 80(16), 7789-7798, (2006).

Hare et al., "Retroviral intasome assembly and inhibition of DNA strand transfer", *Nature* 464, 232-236, (2010).

Himmel et al., "Structure of HIV-1 reverse transcriptase with the inhibitor beta-Thujaplicinol bound at the RNase H active site", *Structure* 17, 1625-1635, (2009).

Klumpp et al. "RNA and DNA hydrolysis are catalyzed by the influenza virus endonuclease", *J Biol Chem.*, 275(9), 6181-6188, (2000).

Memoli et al., "MultiDrug-Resistant 2009 Pandemic Influenza A(H1N1) Viruses Maintain Fitness and Transmissibility in Ferrets", *J Infect Dis.*, 203, 348-357, (2010).

Miyamoto et al., "Thujaplicin-copper chelates inhibit replication of human influenza viruses", *Antiviral Res.*, 39, 89-100, (1998).

Moscona A., "Oseltamivir resistance—disabling our influenza defenses", *N Engl J Med.*, 353(25), 2633-2636, (2005).

Parkes et al., "Use of a pharmacophore model to discover a new class of influenza endonuclease inhibitors", *J Med Chem.*, 46, 1153-1164, (2003).

Rees et al., "Fragment-based lead discovery", *Nat Rev Drug Discov.*, 3, 660-672, (2004).

Taubenberger et al., "Characterization of the 1918 influenza virus polymerase genes", *Nature*, 437, 889-893, (2005).

Tomassini et al., "Inhibition of cap (m7GpppXm)-dependent endonuclease of influenza virus by 4-substituted 2,4-dioxobutanoic acid compounds", *Antimicrob Agents Chemother*, 38(12), 2827-2837, (1994).

Yuan et al., "Crystal structure of an avian influenza polymerase PA(N) reveals an endonuclease active site", *Nature* 458, 909-913, (2009).

Zhao et al., "Nucleoside monophosphate complex structures of the endonuclease domain from the influenza virus polymerase PA subunit reveal the substrate binding site inside the catalytic center", *J Virol.*, 83(18), 9024-9030, (2009).

\* cited by examiner

Figure 5 a

| Designation | Name | Molecular Structure | IC₅₀ (µM) | NHA | -LE |
|---|---|---|---|---|---|
| MB15-7 | 4-(1H-Pyrrol-1-yl) benzylamine | 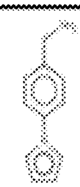 | 100 | 13 | 0.422 |
| MB4-4 | N-[4-(1H-Imidazol-1-yl) benzyl]-N-methylamine | 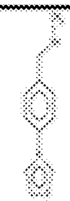 | 100 | 14 | 0.392 |
| MB42-5 | [4-(2-furyl)phenyl] methylamine | 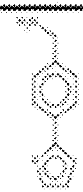 | 150 | 13 | 0.403 |
| MB65-6 | 4-(2-Thienyl) benzylamine | 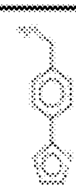 | 200 | 13 | 0.39 |
| MB35-2 | 4-(1,2,3-thiadiazol-4-yl) aniline | 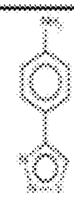 | 500 | 12 | 0.377 |
| MB43-4 | 4-(1H-imidazol-1-yl) phenol | 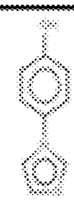 | 1000 | 12 | 0.343 |
| MB51-1 | [4-(1H-pyrazol-1-yl) phenyl]methanol | | 1000 | 13 | 0.316 | a b

US 8,859,290 B2

INHIBITORS OF INFLUENZA ENDONUCLEASE ACTIVITY AND TOOLS FOR THEIR DISCOVERY

CROSS-REFERENCE TO RELATED APPLICATION(S)

This patent application claims the benefit of priority of U.S. application Ser. No. 61/510,731, filed Jul. 22, 2011, which application is herein incorporated by reference.

SEQUENCE LISTING

The instant application contains a Sequence Listing which has been submitted in ASCII format via EFS-Web and is hereby incorporated by reference in its entirety. Said ASCII copy, created on Oct. 11, 2012, is named 08035016US1.txt and is 9,288 bytes in size.

BACKGROUND OF THE INVENTION

Influenza A virus is constantly evolving. Seasonal influenza A infections are effectively prevented by vaccines, which are reformulated each year. Influenza A viruses infect a wide range of avian and mammalian hosts (Lamb et al., 2001). The virus has eight genomic RNA segments; reassortment of genomic RNAs from different strains and subtypes of influenza A is responsible for sporadic emergence of pandemic flu. Alternatively, all eight genomic RNAs may be derived from an avian virus, and such a progenitor virus then undergoes multiple mutations in the process of adapting to a mammalian host (Taubenberger et al., 2005).

The available treatment options for influenza are limited. Current antivirals are directed against the M2 ion-channel protein (adamantanes) and neuraminidase (zanamivir and oseltamivir). The adamantine drugs, amantadane and rimantadine, are ineffective due to emergence of resistance (predominantly through a M2 mutation, S31N) and these drugs, in general, are not in clinical use. The neuraminidase (NA)-inhibiting oral drug, oseltamivir (Tamiflu) is widely used for treating flu. Oseltamivir-resistant seasonal influenza A strains have been circulating for the last few years (Moscona, 2005). The mutant viruses predominantly contain the NA H274Y mutation; when accompanied by compensatory mutations, the mutant viruses exhibit fitness comparable to wild-type influenza A and remain resistant to oseltamivir (Bloom et al., 2010). These mutations can emerge in almost all influenza A subtypes/strains, including the pandemic 2009 H1N1 virus (Memoli et al., 2011), a major concern for an effective treatment of flu. Therefore, new drugs are essential for treating drug-resistant and future pandemic flu strains.

SUMMARY OF THE INVENTION

Accordingly, the present invention provides inhibitors of influenza endonuclease activity and tools for their discovery.

Certain embodiments of the invention provide an isolated or purified amino acid sequence at least 90%, 91%, 92%, 93%, 94% or 95% identical to SEQ ID NO:1. In certain embodiments the sequence is at least 96% identical to SEQ ID NO:1. In certain embodiments the sequence is at least 97% identical to SEQ ID NO:1. In certain embodiments the sequence is at least 98% identical to SEQ ID NO:1. In certain embodiments the sequence is at least 99% identical to SEQ ID NO:1. In certain embodiments the sequence is SEQ ID NO:1.

Certain embodiments of the invention provide an isolated or purified amino acid sequence at least 90%, 91%, 92%, 93%, 94% or 95% identical to SEQ ID NO:2. In certain embodiments the sequence is at least 96% identical to SEQ ID NO:2. In certain embodiments the sequence is at least 97% identical to SEQ ID NO:2. In certain embodiments the sequence is at least 98% identical to SEQ ID NO:2. In certain embodiments the sequence is at least 99% identical to SEQ ID NO:2. In certain embodiments the sequence is SEQ ID NO:2.

In certain embodiments the isolated or purified amino acid sequence is about 200 to about 220 amino acids in length. In certain embodiments the sequence is about 209 amino acids in length.

Certain embodiments of the invention provide an isolated or purified amino acid sequence at least 95% identical to SEQ ID NO:2 that comprises an N-terminal or C-terminal tandem His-tag.

Certain embodiments of the invention are directed to an isolated or purified nucleic acid sequence (e.g. DNA or RNA) encoding an amino acid sequence described herein.

Certain embodiments of the invention are directed to an expression construct comprising a nucleic acid sequence described herein.

Certain embodiments of the invention provide an expression vector comprising a construct described herein.

Certain embodiments of the invention provide a crystal formed from an amino acid described herein.

Certain embodiments of the invention provide a crystal of an endonuclease characterized by the parameters described in Table 1 or 2, wherein the parameters described in Table 1 or 2 can vary by +/−5% (e.g., 1%, 2%, 3%, 4% or 5%). In certain embodiments, the crystal is Form I, Form II or Form III as defined in Table 1 or 2, wherein the parameters described in Table 1 or 2 can vary by +/−5% (e.g., 1%, 2%, 3%, 4% or 5%). In certain embodiments the crystal is Form I. In certain embodiments the crystal is Form II. In certain embodiments the crystal is Form III.

Certain embodiments of the invention provide a method to determine whether a compound inhibits endonuclease activity, comprising contacting the compound with a crystal described herein and determining whether the compound binds the endonuclease at or near the active site in a manner that would inhibit the enzyme. Using the crystal forms described herein, the art worker can consider, e.g., shape, chemical composition, and individual protein-ligand interactions in determining whether the compound binds the endonuclease at or near the active site in a manner that would inhibit the enzyme.

Certain embodiments of the invention provide a method to determine whether a compound inhibits endonuclease activity, comprising contacting the compound with an amino acid described herein and determining whether the compound inhibits the endonuclease activity of the amino acid. Certain embodiments further comprise contacting the compound and amino acid with a single stranded oligonucleotide, wherein the oligonucleotide comprises a fluorophore and a minor groove binder non-fluorescent quencher, and wherein there is a reduced level in fluorescence, as compared to a control (e.g., a compound that does not inhibit endonuclease activity and thereby does not decrease or prevent cleavage). In certain embodiments, the fluorophore is at the 5' end of the oligonucleotide and the minor groove binder non-fluorescent quencher is at the 3' end of the oligonucleotide. In certain embodiments the fluorophore is at the 3' end of the oligonucleotide and the minor groove binder non-fluorescent quencher is at the 5' end of the oligonucleotide. In certain embodiments the oligonucleotide is RNA, DNA or an RNA/DNA hybrid. In certain embodiments the oligonucleotide is RNA. In certain embodiments the oligonucleotide is DNA. In certain embodiments the oligonucleotide comprises between about 10 nucleotides to about 50 nucleotides. In certain embodiments the fluorophore is 6-carboxy-fluorescein.

Certain embodiments of the invention provide a method for promoting an anti-viral effect in vitro or in vivo comprising contacting a sample in need of such treatment with a compound of formula I, II, III, 1-5, or 10-15, or a salt thereof.

Certain embodiments of the invention provide a method of inhibiting a viral infection in an animal, comprising administering an effective amount of a compound of formula I, II, III, 1-5, or 10-15, or a pharmaceutically acceptable salt thereof, to the animal.

Certain embodiments of the invention provide a method of inhibiting a viral infection in an animal, comprising administering an effective amount of a compound of formula:

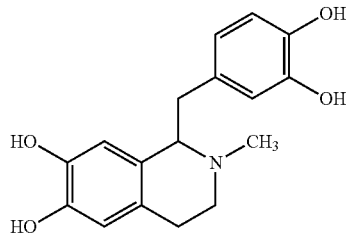 [SMILES: CN1CCc2cc(O)c(O)cc2C1Cc1ccc(O)c(O)c1]

or a pharmaceutically acceptable salt thereof, to the animal.

In certain embodiments the animal is a human.

Certain embodiments of the invention provide a compound of formula I, II, III, 1-5, or 10-15, or a salt thereof, for use in the prophylactic or therapeutic treatment of a viral infection.

Certain embodiments of the invention are directed to the use of a compound of formula I, II, III, 1-5, or 10-15, or a salt thereof, for the manufacture of a medicament for treating a viral infection in an animal.

Certain embodiments of the invention provide a method to inhibit an influenza endonuclease, comprising contacting said endonuclease with a compound of I, II, III, 1-5, or 10-15, or a salt thereof.

In certain embodiments of the invention the viral infection is an influenza infection. In certain embodiments the viral infection is an influenza A, B or C infection. In certain embodiments the viral infection is an influenza A infection.

Certain embodiments of the invention are directed to the use of the crystals described herein for molecular modeling or docking studies.

BRIEF DESCRIPTION OF THE FIGURES

FIG. 4. Schematic representation of the high-throughput fluorescent endonuclease assay described in Example 1. FAM fluoresces when PA$_N$ cleaves the polynucleotide. The result from such an activity assay is shown in FIG. 2a.

DETAILED DESCRIPTION

Influenza A contains eight negative-stranded RNA genomic segments. The three largest genomic RNA segments encode the viral RNA-dependent RNA polymerase (RdRP) proteins consisting of the polymerase acidic protein (PA) and polymerase basic protein 1 (PB1) and 2 (PB2) subunits. The PA subunit: (i) has endonuclease and protease activities, (ii) is involved in viral RNA (vRNA)/complementary RNA (cRNA) promoter binding, and (iii) interacts with the PB1 subunit. PA has two domains, PA$_N$ (a ~25 kDa N-terminal domain; residues 1-197) and PA (~55 kDa C-terminal domain; residues 239-716). Crystal structures of PA$_C$ have been determined in complexes with N-terminal fragments of PB1.

Figure 1:
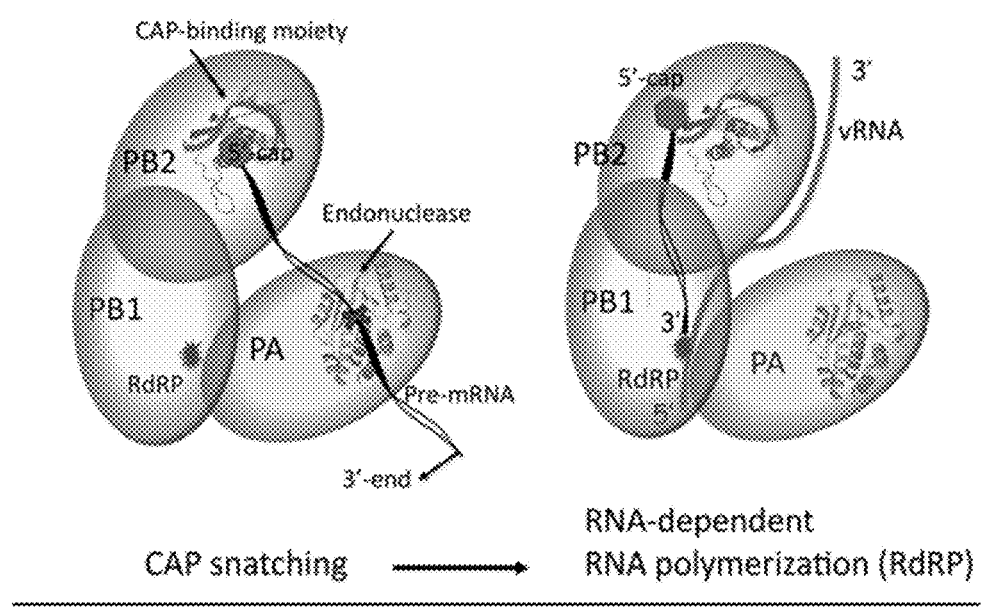
FIG. 1. Schematic representation of viral mRNA transcription by influenza A polymerase. (a) The polymerase PB2 subunit (PB2$_{cap}$; residues 318-482), binds the 5' cap ($^{m7}$GpppNp) of a host pre-mRNA and the pre-mRNA is cleaved 10-13 nucleotides downstream of the cap. (b) Viral transcription starts from the cleaved end of the capped RNA fragment.

The RdRP of influenza A is responsible for the replication and transcription of the viral RNA genes. The viral mRNA transcription involves a cap-snatching mechanism (FIG. 1). Cap snatching is an important event in the life cycle of influenza, and the host cells have no analogous activity. Therefore, inhibitors of cap-snatching would act against all influenza subtypes and strains, including tamiflu-resistant influenza A viruses, and will not interfere with host cell activities.

The complete structure of the viral polymerase has not yet been determined at atomic resolution; however, recent structural studies of parts of the influenza A polymerase (reviewed by Das et al. (2010)) have begun to elucidate the architecture of this complex and started to identify multiple promising target sites for designing new influenza drugs. The crystal structures of the N-terminal domain of PA subunit ($PA_N$) from H5N1 (SEQ ID NO:5) (Yuan et al., 2009) and H3N2 (SEQ ID NO:6) (Dias et al., 2009) viruses established that the $PA_N$ domain contains the endonuclease active site composed of conserved acidic residues E80, D108, and E119 positioned in a deep cleft. Blocking the binding of host pre-mRNAs to the cleft and/or inhibiting the cleavage of the pre-mRNAs would inhibit the synthesis of the viral mRNAs and thereby, inhibit replication of influenza A.

However, critical barriers must be overcome in targeting the endonuclease activity with small molecule drugs. As mentioned above, cap snatching (FIG. 1) is a unique mechanism used by several negative sense ssRNA viruses and is not a part of host cell activities. Earlier drug discovery efforts by pharmaceutical companies, using the concept of a common metal ion-dependent endonuclease reaction mechanism, generated low-μM inhibitors of influenza A endonuclease activity (Tomassini et al., 1994; Parkes et al., 2003). Lack of structural information, unavailability of an influenza A endonuclease assay, inefficient transcription assays, and even lack of fundamental knowledge, such as the location of the endonuclease active site in the trimeric influenza A polymerase, were the apparent hurdles in optimizing the efficacy and potency of those lead compounds. The published structures of $PA_N$ identified a highly conserved active site region that is a suitable target for small molecule inhibitors of influenza A endonuclease activity. However, the H5N1 and H3N2 crystal structure publications claim one- and two-metal dependent phosphodiester-bond cleavage activity, respectively. Also, a completely blocked active site in the H3N2 $PA_N$ (SEQ ID NO:6) structure by a loop from a neighboring molecule (residues 52-62) and partially constrained pre-mRNA-binding track in H5N1 $PA_N$ (SEQ ID NO:5) structure are among the major concerns for the effective use of the published crystal forms in structure-based drug design. Unavailability of an inhibitor-bound structure, after the initial reports of $PA_N$ structures in 2009, is indicative of potential problems in using the reported crystal forms for structure-based drug design.

As described herein, the $PA_N$ domain of 2009 H1N1 (swine flu) virus polymerase (SEQ ID NO:2) has now been crystallized in three distinct forms (Table 1). These new crystal forms provide the putative ssRNA-binding cleft that is not positionally constrained by crystal packing, and therefore, the crystal forms are suitable for structurally characterizing $PA_N$: substrate complexes. These crystals were obtained (i) with the active site chelating metal ions (Form I and III; Table 1) and (ii) with no metal ion present at the active site (Form II). Therefore, these crystals are highly relevant for studying the catalytic mechanism of pre-mRNA cleavage by $PA_N$, and for screening for the binding of small molecule inhibitors, both metal-ion chelators and non-chelators. The inhibitor-bound $PA_N$ structures will define the target sites for structure-based design of influenza A cap-snatching inhibitors.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

Compounds for Use in the Methods of the Invention

Compounds which are useful in the practice of the methods of the invention include compounds of formula I, II, III, 1-5, and 10-15 described below as well as salts thereof.

For example, a compound that is useful in the practice of the methods of the invention is a compound of formula I:

wherein:

X is a bond or a ($C_1$-$C_6$)alkyl chain wherein one or two carbon atoms in the chain are optionally replaced by O, S, or $NR_X$, and which chain is optionally substituted on carbon with one or more halo or oxo;

$R^1$ is $R_a$, $R_b$, or $R_c$;

$R^2$ is H or ($C_1$-$C_6$)alkyl;

each $R^3$ is independently hydroxy, halo, cyano, nitro, trifluoromethyl, trifluoromethoxy, carboxy, ($C_1$-$C_6$)alkoxy, ($C_1$-$C_6$)alkoxycarbonyl, ($C_1$-$C_6$)alkanoyloxy, or $NR_dR_e$;

$R^4$ is H, halo, or ($C_1$-$C_6$)alkyl;

$R^5$ is H, halo, or ($C_1$-$C_6$)alkyl;

$R_a$ is phenyl which is substituted with two or more hydroxy and which is also optionally substituted with one or two groups independently selected from hydroxy, halo, cyano, nitro, trifluoromethyl, trifluoromethoxy, carboxy, ($C_1$-$C_6$)alkyl, ($C_1$-$C_6$)alkoxy, ($C_1$-$C_6$)alkoxycarbonyl, ($C_1$-$C_6$)alkanoyloxy, or $NR_dR_e$;

$R_b$ is a five-membered heteroaryl ring which is substituted with a phenyl ring that is optionally substituted with one or more groups independently selected from hydroxy, halo, cyano, nitro, trifluoromethyl, trifluoromethoxy, carboxy, ($C_1$-$C_6$)alkyl, ($C_1$-$C_6$)alkoxy, ($C_1$-$C_6$)alkoxycarbonyl, ($C_1$-$C_6$)alkanoyloxy, or $NR_dR_e$, wherein each ($C_1$-$C_6$)alkyl is optionally substituted with one or more hydroxy, halo, cyano, nitro, trifluoromethyl, trifluoromethoxy, carboxy, ($C_1$-$C_6$)alkyl, ($C_1$-$C_6$)alkoxy, ($C_1$-$C_6$)alkoxycarbonyl, ($C_1$-$C_6$)alkanoyloxy, or $NR_dR_e$;

$R_c$ is a phenyl ring that is substituted with a five-membered heteroaryl ring and that is optionally substituted with one or more groups independently selected from hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$, wherein each $(C_1-C_6)$alkyl is optionally substituted with one or more hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$;

each $R_d$ and $R_e$ is independently H or $(C_1-C_6)$alkyl;

n is 0, 1, 2, 3, or 4; and $R_X$ is H or $(C_1-C_6)$alkyl;

or a salt thereof.

In one specific embodiment of the invention X is a bond or $CH_2$.

In one specific embodiment of the invention $R^1$ is phenyl which is substituted with two or more hydroxy and which is also optionally substituted with one or two groups independently selected from hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$.

In one specific embodiment of the invention $R^1$ is a five-membered heteroaryl ring which is substituted with a phenyl ring that is optionally substituted with one or more groups independently selected from hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$, wherein each $(C_1-C_6)$alkyl is optionally substituted with one or more hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$.

In one specific embodiment of the invention $R^1$ is a phenyl ring that is substituted with a five-membered heteroaryl ring and that is optionally substituted with one or more groups independently selected from hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$, wherein each $(C_1-C_6)$alkyl is optionally substituted with one or more hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$.

In one specific embodiment of the invention the compound of formula I is a compound of formula Ia:

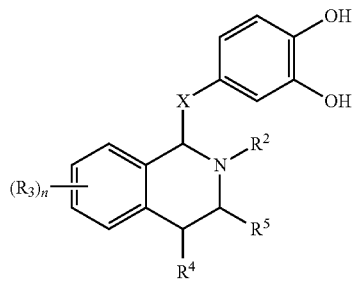

(Ia)

or a salt thereof.

In one specific embodiment of the invention, for a compound of formula Ia, X is a bond or $CH_2$.

In one specific embodiment of the invention the compound of formula I is a compound of formula Ib:

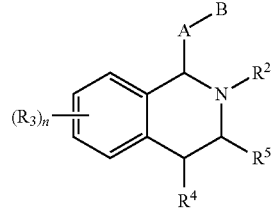

(Ib)

wherein:

A is a five-membered heteroaryl ring; and

B is a phenyl ring that is optionally substituted with one or more groups independently selected from hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$, wherein each $(C_1-C_6)$alkyl is optionally substituted with one or more hydroxy, halo, cyano, nitro, trifluoromethyl, trifluoromethoxy, carboxy, $(C_1-C_6)$alkyl, $(C_1-C_6)$alkoxy, $(C_1-C_6)$alkoxycarbonyl, $(C_1-C_6)$alkanoyloxy, or $NR_dR_e$;

or a salt thereof.

In one specific embodiment of the invention for a compound of formula Ib, -A-B taken together is selected from:

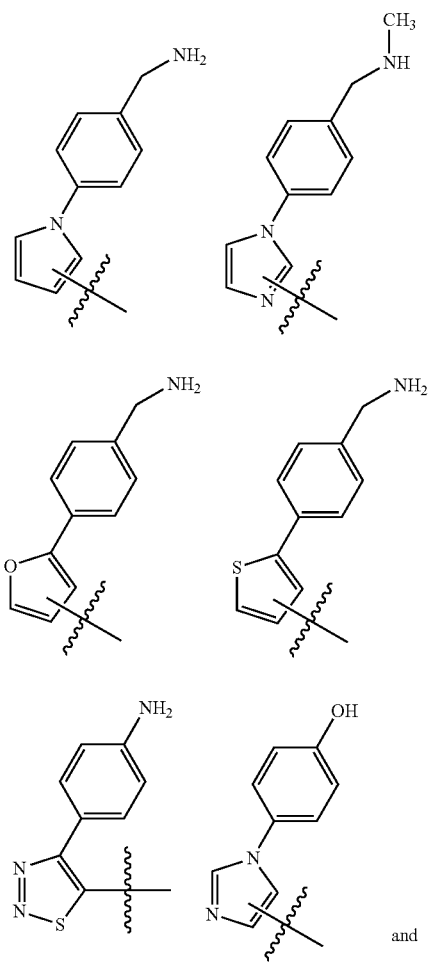

and

-continued

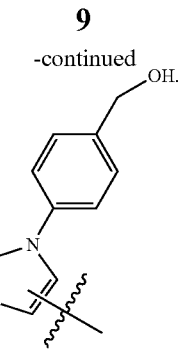

In one specific embodiment of the invention the compound of formula I is a compound of formula Ic:

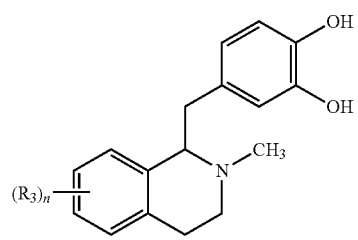

(Ic)

or a salt thereof.

In one specific embodiment of the invention the compound of formula I is a compound which is:

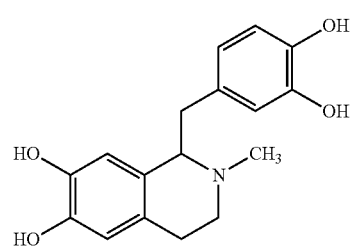 [SMILES: CN1CCc2cc(O)c(O)cc2C1Cc1ccc(O)c(O)c1]

or a salt thereof.

Another compound that is useful in the practice of the methods of the invention is a compound of Formula (II), which is a five-membered heteroaryl ring which is substituted with a phenyl ring that is optionally substituted with one or more groups independently selected from hydroxy, halo, cyano, nitro, trifluoromethyl, trifluoromethoxy, carboxy, ($C_1$-$C_6$)alkyl, ($C_1$-$C_6$)alkoxy, ($C_1$-$C_6$)alkoxycarbonyl, ($C_1$-$C_6$)alkanoyloxy, or $NR_dR_e$, wherein each ($C_1$-$C_6$)alkyl is optionally substituted with one or more hydroxy, halo, cyano, nitro, trifluoromethyl, trifluoromethoxy, carboxy, ($C_1$-$C_6$)alkyl, ($C_1$-$C_6$)alkoxy, ($C_1$-$C_6$)alkoxycarbonyl, ($C_1$-$C_6$)alkanoyloxy, or $NR_dR_e$; or a salt thereof.

Another compound that is useful in the practice of the methods of the invention is a compound of formula (III):

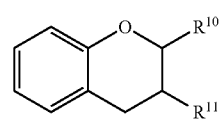

wherein:

$R^{10}$ is phenyl; and $R^{11}$ is hydroxy or benzoyloxy;

wherein the compound is optionally substituted with one or more hydroxy;

or a salt thereof.

In one specific embodiment of the invention the compound of formula III is a compound of formula (IIIa):

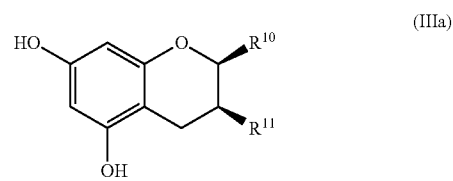

(IIIa)

or a salt thereof.

In one specific embodiment of the invention the compound of formula III is a compound of formula (IIIb):

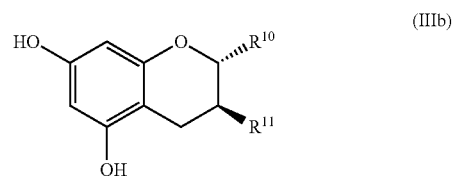

(IIIb)

or a salt thereof.

In one specific embodiment of the invention, for a compound of formula III, $R^{10}$ is 3,4-dihydroxyphenyl or 3,4,5-trihydroxyphenyl.

In one specific embodiment of the invention, for a compound of formula III, $R^{11}$ is hydroxy or 3,4,5-trihydroxybenzoyloxy.

In one specific embodiment of the invention, the compound of formula III is selected from:

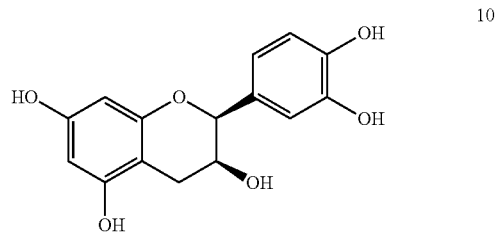

10

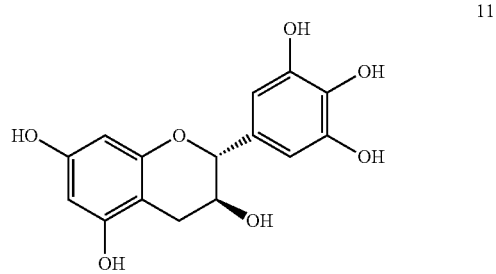

11

-continued

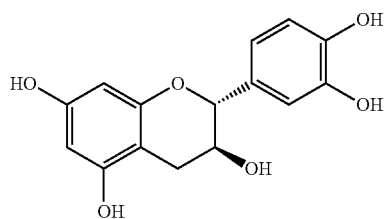

12

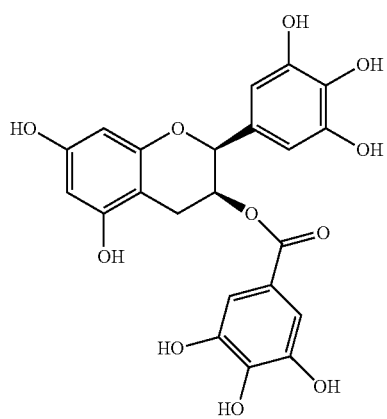

13

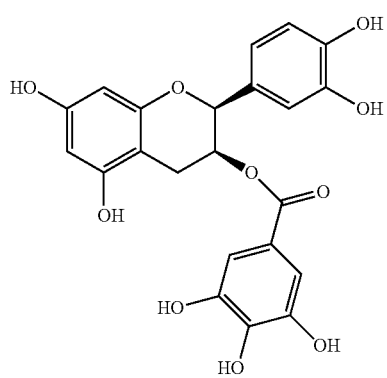

14

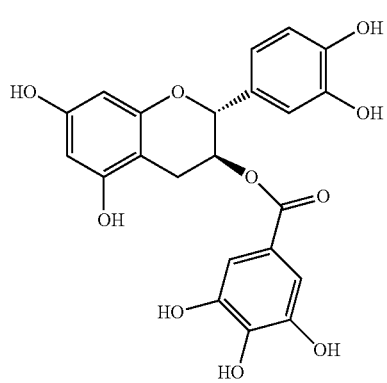

15 and salts thereof.

Other compounds which are useful in the practice of the methods of the invention include compounds of formula 1-5:

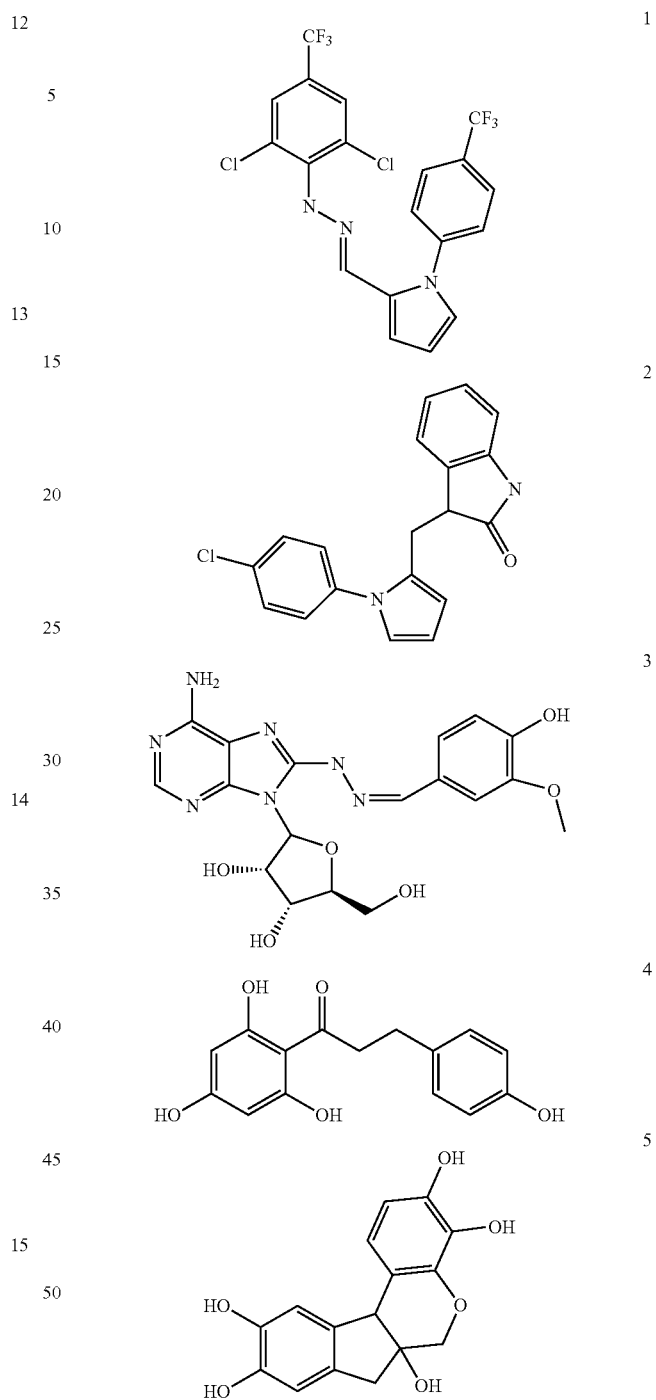

and salts thereof.

The invention also provides a pharmaceutical composition comprising a compound of formula I, II, III, 1-5 or 10-15, or a pharmaceutically acceptable salt thereof, and a pharmaceutically acceptable diluent or carrier.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diasteromer. In another embodiment, a compound of the invention may be at least 51% a single diasteromer. In another embodiment, a compound of the invention may be at least 60% a single diastereomer. In another embodiment, a compound of the invention may be at least 70% a single diasteromer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In cases where compounds are sufficiently basic or acidic, a salt of a compound of formula I, II, III, 1-5 or 10-15 can be useful as an intermediate for isolating or purifying a compound of formula I, II, III, 1-5 or 10-15. Additionally, administration of a compound of formula I, II, III, 1-5 or 10-15 as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I, II, III, 1-5 or 10-15 can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I, II, III, 1-5 or 10-15 to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I, II, III, 1-5 or 10-15 can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleotide sequences: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C.

(aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

Figure 5:
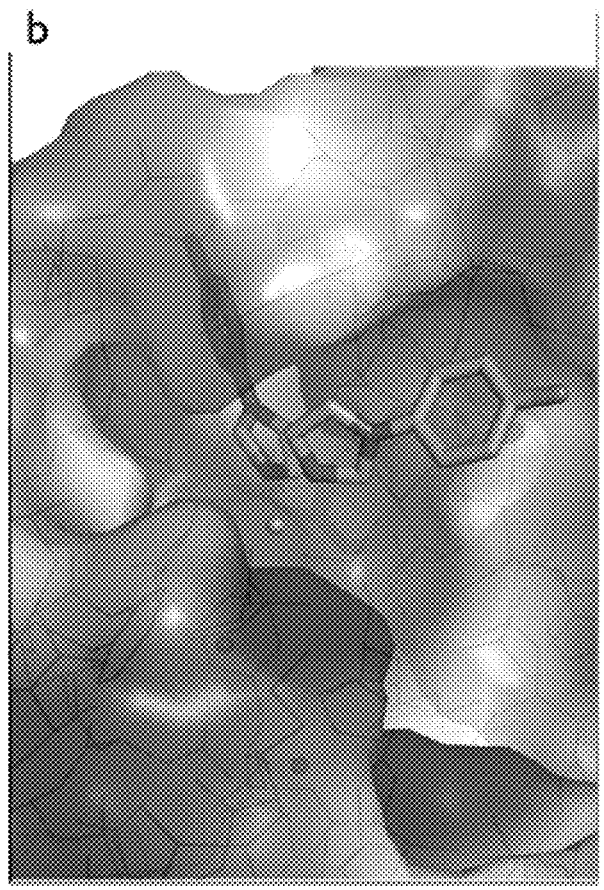
FIG. 5. MB43-4 like inhibiting compounds. (a) Table of MB43-4 like compounds that inhibit the endonuclease. (b) X-ray crystal structure of MB43-4 bound to 2009 pandemic H1N1 endonuclease (SEQ ID NO:2). The protein has an electrostatic surface with both positively and negatively charged regions. The active site metals are depicted as spheres. (c) Structure with 3Fo-2Fc density shown around MB43-4 and the active site metals. The metal-binding site induced by fragment binding is shown as a light gray sphere and indicated with an arrow. Arrows point to two additional metal binding sites, which are depicted as dark gray spheres.
Figure 5:
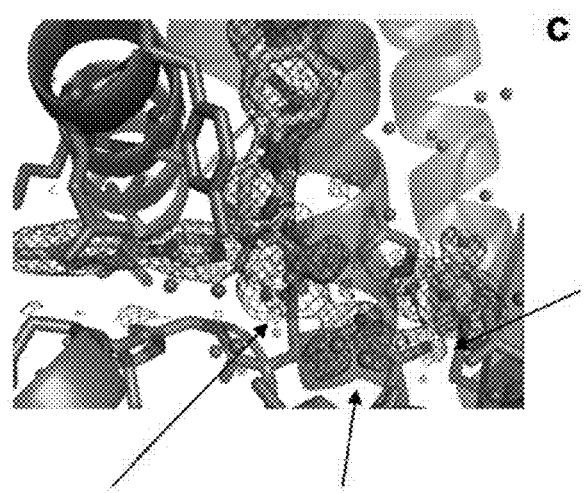

The ability of a compound of the invention to act as influenza endonuclease inhibitors may be determined using pharmacological models which are well known to the art, or using the assays described in Example 1 below. Experimental results from these assays for representative compounds of the invention are discussed herein, for example, in Example 1 and shown in FIGS. 5 and 6. These results demonstrate that compounds of the invention may be useful as influenza endonuclease inhibitors. Accordingly, compounds of the invention may be useful as therapeutic agents for the treatment of viral infections, such as influenza A. Additionally, compounds of the invention may be useful as pharmacological tools for the further investigation of influenza endonuclease structure and function.

The invention will now be illustrated by the following non-limiting Example.

Example 1

Inhibitors of Influenza Endonuclease Activity and Tools for their Discovery

An H1N1 influenza A endonuclease expression construct has now been developed, which was used to produce three novel crystal forms based on optimized crystallization conditions. Additionally, a new high throughput enzymatic assay was also developed. Using these materials and techniques, commercially available libraries of drug-like compounds were screened and novel inhibitors of the influenza A enzyme were discovered. The binding sites and the binding modes of the compounds were characterized, and several new compounds that are expected to have improved inhibition were modeled. New compounds based on the above information may be synthesized and tested and these inhibitors may be developed into drugs for the current and future strains of influenza.

Results

A. Crystal Structures of a Catalytically Active $PA_N$ Domain of 2009 Pandemic H1N1 (Swine Flu) Polymerase (SEQ ID NO:2).

Figure 2:
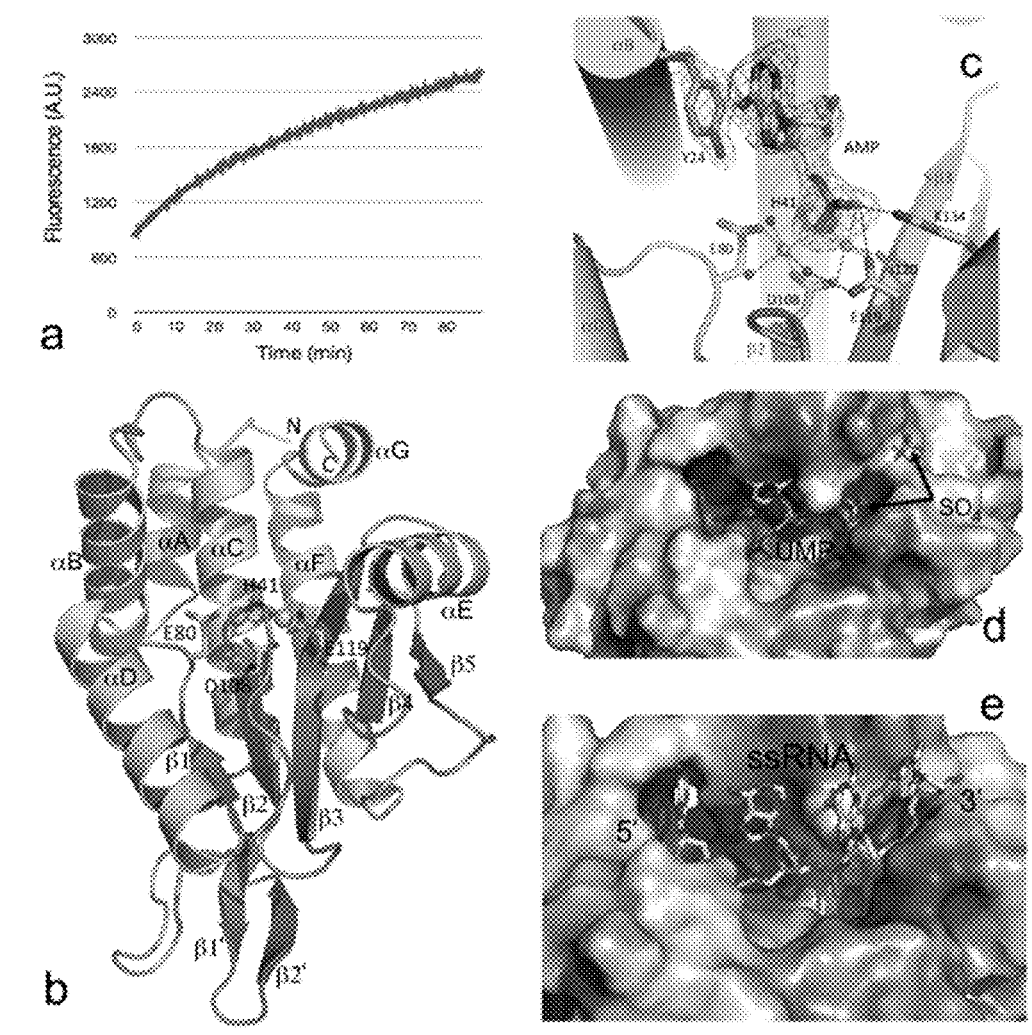
FIG. 2. The structure and activity of 2009 pandemic H1N1 PA$_N$ domain (SEQ ID NO:2). (a) A fluorescence-based assay described in Example 1 shows endonuclease activity of H1N1 PA$_N$ (SEQ ID NO:2); fluorescence increases as oligonucleotides are cleaved by PA$_N$. (b) Structure of the H1N1 PA$_N$ (SEQ ID NO:2) revealed the presence of a β-hairpin ((β1'-β2') that contains residue G58, conserved in influenza A, B, and C. (c) Electron density showing the binding of AMP to PA$_N$ (SEQ ID NO:2). (d) Binding of nucleoside monophosphate and SO$_4^{2-}$ ions in the structure predicts the pre-mRNA binding track. (e) Modeled ssRNA binding to H1N1 PA$_N$ (SEQ ID NO:2); this proposed model is different from that proposed for H5N1 PA$_N$ (SEQ ID NO:5). Electrostatic potential surfaces of H1N1 PA$_N$ (SEQ ID NO:2) are shown in panels (d) and (e).

The crystal structures of a catalytically active (FIG. 2a) $PA_N$ domain of 2009 pandemic H1N1 polymerase (SEQ ID NO:2) has been obtained. Use of a crystallization robot, followed by manual optimization of crystallization hits, three distinct crystal forms were elucidated (Table 1). A typical resolution of the structures in any of the three crystal forms is 2 Å or better. Unlike the previously determined $PA_N$ structures, the entire polypeptide chain of H1N1 $PA_N$ (SEQ ID NO:2) could be traced; its structure revealed the presence of an additional β-hairpin composed of β1' and β2' strands (FIG. 2b). Apart from this newly discovered β-hairpin, the five-stranded β-sheet and seven α helices superimposed well on respective structural elements of H3N2 (SEQ ID NO:6), and 115N1 $PA_N$ (SEQ ID NO:5) structures; however, unlike in H3N2 and H5N $PA_N$ crystal structures, H1N1 $PA_N$ (SEQ ID NO:2) has no crystal contact interfering with the putative binding site for ssRNA or with the endonuclease active site region. These H1N1 crystal forms are ideal for obtaining structures of various complexes of $PA_N$ (SEQ ID NO:2) including ssRNA-bound pre- and post-catalytic complexes. Structures of $PA_N$ (SEQ ID NO:2) in complexes with each of the four nucleoside-monophosphates, and with two known endonuclease inhibitors, were obtained after optimizing the soaking conditions for Form I crystals.

TABLE 1

Crystal forms of $PA_N$ domain of 2009 pandemic H1N1 influenza A polymerase (SEQ ID NO: 2).

| Space Group | Form I<br>C222$_1$ | Form II<br>P2$_1$ | Form III<br>C2 |
|---|---|---|---|
| Unit cell parameters (a, b, c in Å; α, β, γ in °) | 86.66-90.86, 100.83-102.94, 65.95-66.62; 90, 90, 90 | 63.61-64.97, 65.44-66.78, 64.22-65.95; 90, 112.66-114.73, 90 | 102.507, 89.248, 132.613; 90, 90, 90 |
| Resolution (Å) | 40-1.63 | 40-2.0 | 40-1.9 |
| Numbers of molecules/ asymmetric unit | 1 | 2 | 4 |
| Remarks | Two Mn (II) ions are present at the active site. | No metal ion present at the active site. | Two metal ions present at the active site. Twinned data - twinning fraction 0.5; operator -h, -k, l |

Crystal forms I, II and III are characterized by the parameters listed in Table 1 above. Accordingly, certain embodiments are directed towards crystals having combinations of such characteristics.

B. Defining the Binding Sites for Inhibitors of Influenza A Endonuclease Activity, and Target the Sites for Drug Design.

The endonuclease/cap snatching activity of influenza A polymerase provides a valuable target for developing new flu drugs. Reported crystal structures of $PA_N$ (Yuan et al., 2009; Dias et al., 2009) have identified the endonuclease active site; however no structure of $PA_N$ is available in complex with an endonuclease inhibitor. A recent report on structures of H5N1 $PA_N$ (SEQ ID NO:5) in complexes with three different nucleoside monophosphates bound at the active site (Zhao et al., 2009) unexpectedly showed significant differences in their binding modes; the sugar rings were positioned differently in each structure. This result is somewhat surprising because, like in other endonuclease enzymes, $PA_N$ is expected to have a common mode of binding to sugar-phosphate backbone of NMPs at the active site. Additionally, defining the mode of binding of known endonuclease inhibitors to $PA_N$ and discovery of new sites for inhibitor binding are essential for initiating designs of endonuclease-inhibiting flu drugs.

Figure 3:
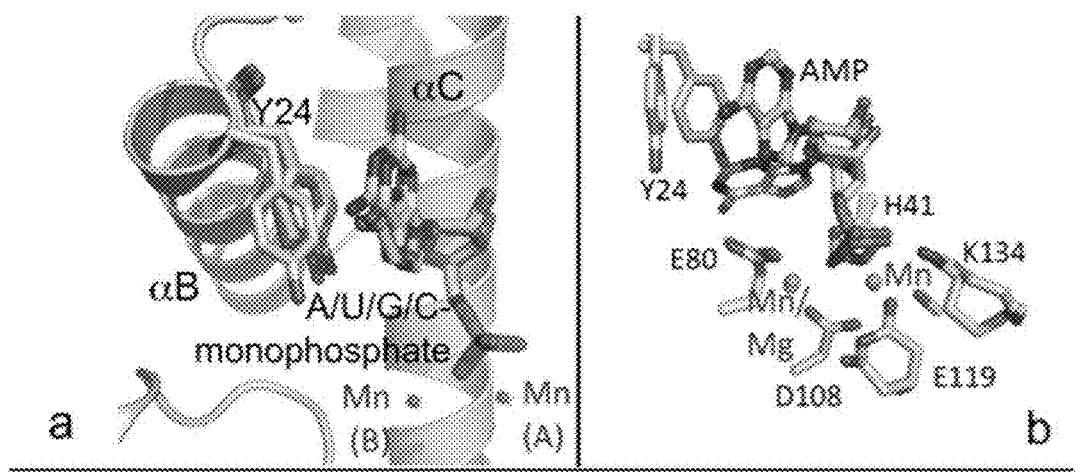
FIG. 3. The binding of nucleoside monophosphates to 2009 H1N1 PA$_N$ (SEQ ID NO:2). (a) Superposition of crystal structures of PA$_N$ (SEQ ID NO:2) in complexes with four different nucleoside (A, U, G, C) monophosphates. The compounds chelate two Mn (II) ions at the endonuclease active site and the bases are stacked with the aromatic side chain of Y24; the side chain of Y24 is repositioned upon binding a nucleoside monophosphate compared to its position in apo PA$_N$. (b) Comparison of the modes of binding of AMP to H1N1 PA$_N$ (SEQ ID NO:2) (AMP stacks with Tyr24) and H5N1 PA$_N$ (SEQ ID NO:5) (AMP does not base stack with Tyr24).

The conditions for soaking NMPs into Form I (Table 1) H1N1 $PA_N$ crystals (SEQ ID NO:2) were optimized and the structures of $PA_N$ in complexes with NMPs (AMP, GMP, UMP, and CMP) at resolutions ranging between 2.00-1.65 Å (Table 2) were determined. The NMPs chelate two $Mn^{2+}$ ions at the active site. Superposition of the four structures of $PA_N$ (SEQ ID NO:2):NMP complexes demonstrate that the bound NMPs overlay on each other and share common modes of interactions with $PA_N$ and metal coordination (FIG. 3a). All the NMPs have base stacking with the aromatic side chain of Y24 (FIG. 2c), a highly conserved residue in influenza A, B, and C viruses. There are rare occurrences of phenylalanine or histidine at position 24; neither mutation would preclude the base stacking with NMPs, as F24 or H24 would still maintain the observed base stacking. This common mode of binding of NMPs is different (FIG. 3b) than those reported binding to H5N1 $PA_N$ (SEQ ID NO:5) (Zhao et al., 2009). The difference may be because Y24 is constrained by the intermolecular crystal contacts in the H5N1 $PA_N$ (SEQ ID NO:5) structures. Evaluation of electron density maps calculated using the deposited PDB coordinates and structure factors of H5N1 $PA_N$ (SEQ ID NO:5):NMP complexes (PDB IDs. 3HW3 and 3HW5) suggested that a hydrophobic small molecule is sandwiched between the aromatic side chains of Y24 and W88, of a neighboring molecule. Analysis suggests that the conformational restraint on Y24 by crystal packing did not permit Y24 to base-stack with NMPs in the structures of H5N1 $PA_N$ (SEQ ID NO:5):NMP complexes. The active site cleft is completely blocked in H3N2 $PA_N$ (SEQ ID NO:6) structure, and therefore the crystal system is not suitable for structural studies of $PA_N$:substrate/inhibitor complexes. In contrast, the crystal system showed rearrangement of the Y24 side chain upon comparison of the structures of H1N1 $PA_N$ (SEQ ID NO:2) in the presence and absence of a NMP (FIG. 3a). This flexibility of the active site region appears to be important for the binding of ssRNA, NMPs, and endonuclease inhibitors. In fact, the conformational switching of Y24 allowed the endonuclease inhibitors to bind to $PA_N$ (SEQ ID NO:2) as discussed below.

TABLE 2

Crystal forms of the 2009 pandemic H1N1 influenza A polymerase $PA_N$ domain (SEQ ID NO: 2) unliganded and in complex with NMPs and inhibitors.

| Complex | Cell parameters (a, b, c in Å; α, β, γ in °) | Resolution (in Å) | $R_{Free}$ | $R_{Work}$ |
|---|---|---|---|---|
| Apo (Form I) | 88.28, 102.06, 66.26; 90.00, 90.00, 90.00 | 1.63 | 0.170 | 0.201 |
| Form II | 65.38, 66.91, 66.14; 90.00, 115.34, 90.00 | 2.00 | 0.189 | 0.227 |
| Form III | 102.51, 89.25, 132.61; 90.00, 89.98, 90.00 | 1.90 | 0.210 | 0.232 |
| AMP | 88.45, 101.45, 66.18; 90.00, 90.00, 90.00 | 2.00 | 0.206 | 0.223 |
| CMP | 88.62, 101.80, 66.21; 90.00, 90.00, 90.00 | 1.80 | 0.165 | 0.199 |
| GMP | 88.91, 102.11, 66.20; 90.00, 90.00, 90.00 | 1.74 | 0.168 | 0.194 |
| UMP | 88.46, 101.77, 66.23; 90.00, 90.00, 90.00 | 1.80 | 0.160 | 0.210 |
| MB43-4 | 86.57, 102.71, 66.19; 90.00, 90.00, 90.00 | 1.64 | 0.179 | 0.196 |
| D,L-Laudanosoline | 90.63, 101.30, 65.74; 90.00, 90.00, 90.00 | 1.80 | 0.209 | 0.227 |

Crystal forms I, II and III are characterized by the parameters listed in Table 2 above. Accordingly, certain embodiments are directed towards crystals having combinations of such characteristics.

C. Endonuclease Activity Assay.

Figure 4:
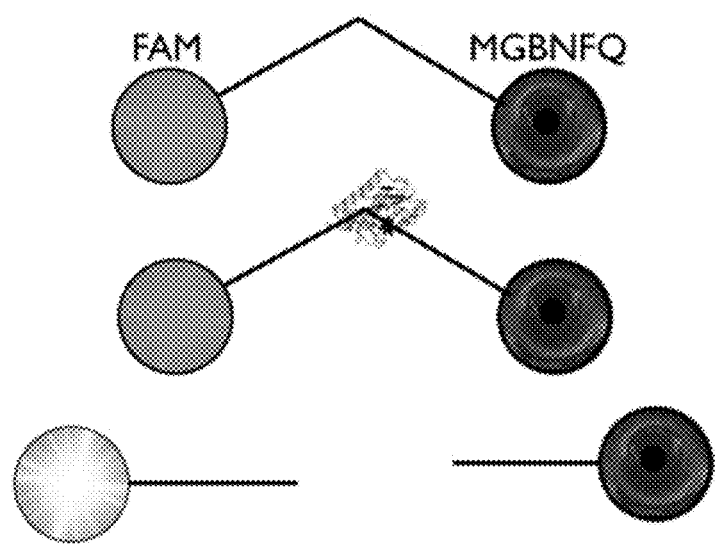

The $PA_N$ domain has been shown to cleave ssRNA as well as ssDNA (Klumpp et al., 2000). To demonstrate the inhibition of endonuclease cleavage by $PA_N$, a high throughput assay was developed. In the assay, a TaqMan-like oligonucleotide containing a 6-carboxy-fluorescein (FAM) fluorophore at the 5'-end followed by 19 nucleotides and a minor groove binding non-fluorescent quencher (MGBNFQ, Applied Biosystems) at the 3'-end (FIG. 4) was used. When excited by a real-time PCR machine's light source, MGBNFQ quenches the fluorescence of FAM via fluorescence resonance energy transfer. If the endonuclease cleaves the oligonucleotide, the quencher is no longer coupled to the fluorophore, and therefore, FAM fluoresces. This assay is performed in a high-throughput 96 well plate format. The assay is used to evaluate the inhibitory characteristics of compounds that are found to bind $PA_N$, and to screen libraries of drug-like compounds.

D. Screening for Binding of Drug-Like Fragments to $PA_N$ for Discovering New Classes of Endonuclease Inhibitors.

Fragment screening has been proven to be a valuable tool for discovering potent small molecule inhibitors (Congreve et al., 2008). When used in conjunction with X-ray crystallography, a crystal of the protein of interest is soaked with a mixture or "cocktail" of small organic molecules of size 100-300 Da. The soaked crystal is then subjected to X-ray diffraction analysis and experimental electron density maps detect the binding of fragments. Typically, screening a properly designed library of chemically diverse compounds can discover sites on the protein with affinity to different chemical groups. Although fragments may have relatively low binding affinity (in the range of hundreds of µM to mM) to a protein, they can be used as powerful probes to map the binding sites of the protein as well as provide a chemically diverse platform for lead development. Fragment screening provides a highly efficient way for sampling chemical space without the need for generating costly and complex diversity-oriented combinatorial libraries. Expansion of the fragment hits to lead can use medicinal chemistry and ADME considerations which is an advantage compared to typical leads acquired by high throughput screening (HTS) (Rees et al., 2003). An initial lead discovered by fragment screening increases the likelihood of producing compounds that are inexpensive to synthesize and have favorable pharmacokinetics.

E. New Endonuclease Inhibitors

MB43-4 Like Inhibitor.

Several new types of inhibitors have been found. Structural evidence indicates that certain new compounds bind to the cap snatching protein. These structures also aided in discovering novel target sites of the enzyme. Two types are the 4-(1H-imidazol-1-yl)phenol like compounds (FIG. 5) and laudanosoline (FIG. 6). 4-(1H-imidazol-1-yl)phenol (MB43-4) binds at two locations creating a new metal binding location in the $PA_N$ (SEQ ID NO:2) active site. Binding site 1 is inside a tunnel created by the side chains of Glu23 and Arg84 and coordinates Mn ion chelating with Glu80. Binding site 2 has interactions with the new metal site, Tyr24 and Glu26. The $IC_{50}$ value for MB43-4 is 1 mM giving it a ligand efficiency (LE) of 0.34 kcal/mol·NHA. LE is a measure of binding per non-hydrogen atom of a ligand to its target protein and can be a useful binding metric for fragments. Derivatives of MB43-4 have significantly stronger $IC_{50}$ with MB15-7 and MB4-4 having 0.1 mM $IC_{50}$ levels. Structures with these compounds will be obtained, as well as, using NMR to verify the mode of binding of the strongest inhibitors.

Laudanosoline.

Figure 6:
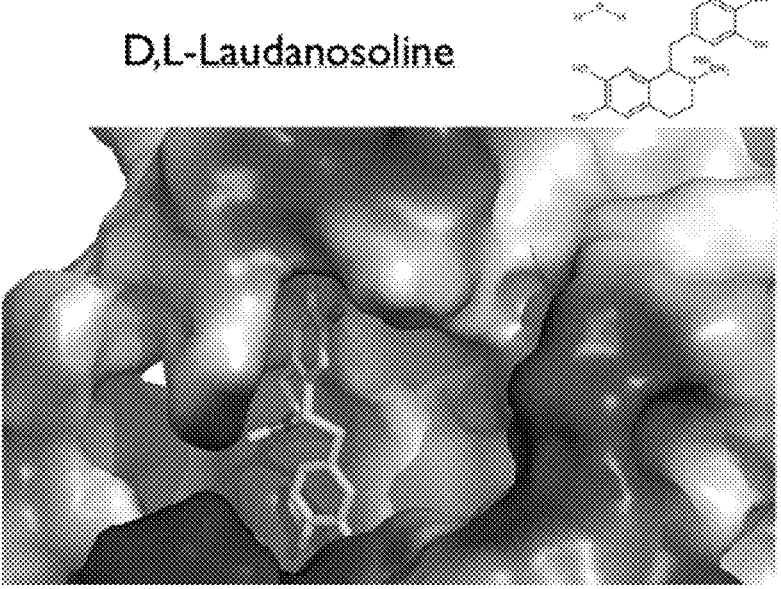
FIG. 6. X-ray crystal structure of D,L-laudanosoline bound to 2009 pandemic H1N1 endonuclease (SEQ ID NO:2). (a) The protein has an electrostatic surface with both positively and negatively charged regions. (b) Structure with 3Fo-2Fc density shown around D,L-laudanosoline and the active site metals are depicted as spheres and indicated with arrows.
Figure 6:
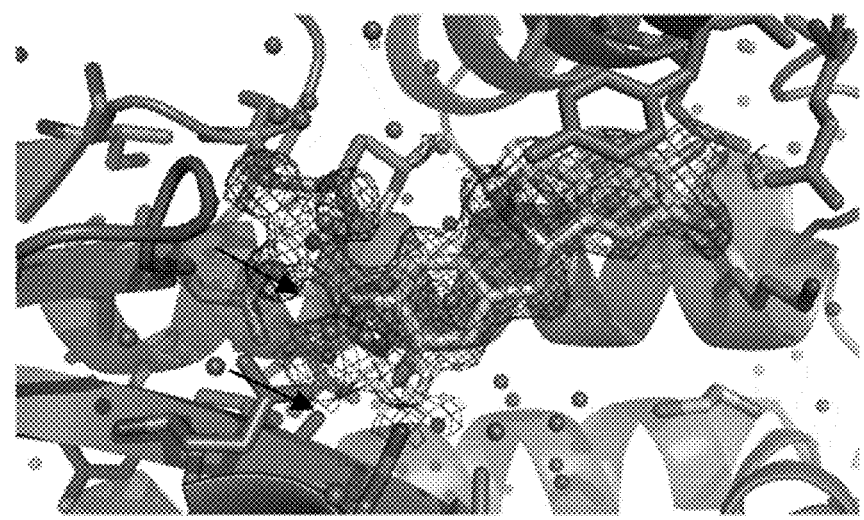

The strongest binding novel compound found by fragment screening is laudanosoline (FIG. 6). The compound catechol interacts with the two active site metals and the quinolone makes π-π stacking interactions with Tyr24 and hydrogen bond interactions with Glu26. The compound was tested as D,L racemic mixture although only the D form is bound, as revealed by experimental electron density maps. The $IC_{50}$ value for laudanosoline is 2 micromolar giving it a LE of at least 0.37 kcal/mol·NHA. The exact value is unknown since it is a racemic mixture of unknown proportions.

F. Structural Studies and Modeling to Map the Endonuclease Inhibitor-Binding Sites Structural studies and molecular modeling will be used to map endonuclease inhibitor-binding sites. Computational techniques will be used to predict new endonuclease inhibitors by screening virtual libraries of compounds in receptor-based and pharmacophore-based models of binding sites. The hit compounds will be experimentally validated (i) by determining crystal structures of the compounds in complexes with $PA_N$ and (ii) for inhibition by enzymatic and virus inhibition assays.

Docking of Virtual Libraries of Compounds into the Inhibitor-Binding Pockets.

The active site pocket conformations, with or without metal ions present, will be used for in silico docking of virtual libraries of compounds. The binding of compounds to $PA_N$ and inhibition will be experimentally verified by structural studies of $PA_N$:inhibitor complexes and in enzymatic assays, respectively.

Structural and Enzymatic Studies of Computationally Predicted Compounds.

The molecules predicted by either receptor-based or pharmacophore-based techniques will be cross verified. The best hits from molecular docking will be manually evaluated by visual inspection for their binding modes and interactions. Compounds that are difficult to synthesize and that have predicted unfavorable ADME properties will be identified at early stages of lead development. Structural and computational studies will help in understanding the adaptability of pockets in $PA_N$ and designing appropriate adaptive inhibitors with essential torsional flexibilities, and utilizing these flexible pocket/ligand characteristics in proposed docking experiments. Selected molecules will be purchased from commercial venders and will be used in structural studies in complexes with $PA_N$ and in enzyme assays as described herein.

G. Plaque Assay to Test Virus Inhibition

Compounds may be tested for inhibition of influenza A virus growth using the plaque assay described herein. The two assays in MDCK cells described below may be used to determine the antiviral activities against influenza virus in tissue culture. Influenza A/Udorn/72 virus may be used for these experiments. In the first assay, the plaque reduction assay, monolayers of MDCK cells will be infected with approximately 100 plaque-forming units (pfu) of the virus, and after virus adsorption, the cells will be overlaid with agar containing a concentration of a compound ranging from 0.1 to 25 micrograms/ml. The assays will be set up in duplicate plates, and the plaques will be counted and compared to the number of plaques in a control experiment lacking any compound. Compounds that cause plaque reduction will be tested in multiple-cycle growth experiments in a second assay. In this assay, MDCK cells will be infected with 0.001 pfu/cell, and after virus adsorption, the inhibitors at various concentrations will be added, and virus yields will be measured by plaque assays at 24, 36, and 48 hours post-infection. The kinetics of virus replication in the presence of an inhibitor will be compared to the kinetics in the absence of the inhibitor.

Methods

A. Protein Expression and Crystallization

The three crystal forms were produced using the same protein construct S2C. S2C (SEQ ID NO:1) was produced by mutagenesis of H5N1 $PA_N$ sequence (SEQ ID NO:5) to match the H1N1 2009 pandemic sequence (PA 1-204). Mutagenesis was performed using overlap extension PCR and ligation independent cloning into a pCDF2 vector (Novagen).

The protein sequence for S2C is:

```
                                              (SEQ ID NO: 1)
MAHHHHHHSRAWRHPQFGGHHHHHHALEVLFQGPLGSMEDFVRQCFNP

MIVELAEKAMKEYGEDPKIETNKFAAICTHLEVCFMYSDFHFIDERGE

SIIVESGDPNALLKHRFEIIEGRDRIMAWTVVNSICNTTGVEKPKFLP

DLYDYKENRFIEIGVTRREVHIYYLEKANKIKSEKTHIHIFSFTGEEM

ATKADYTLDEESRARIKTRLFTIRQEMASRSLWDSFRQSERGEETVEER.
```

The protein sequence after HRV-14 3C protease cleavage is:

```
                                              (SEQ ID NO: 2)
GPLGSMEDFVRQCFNPMIVELAEKAMKEYGEDPKIETNKFAAICTHLE

VCFMYSDFHFIDERGESIIVESGDPNALLKHRFEIIEGRDRIMAWTVV

NSICNTTGVEKPKFLPDLYDYKENRFIEIGVTRREVHIYYLEKANKIK

SEKTHIHIFSFTGEEMATKADYTLDEESRARIKTRLFTIRQEMASRSL

WDSFRQSERGEETVEER.
```

Figure 7:
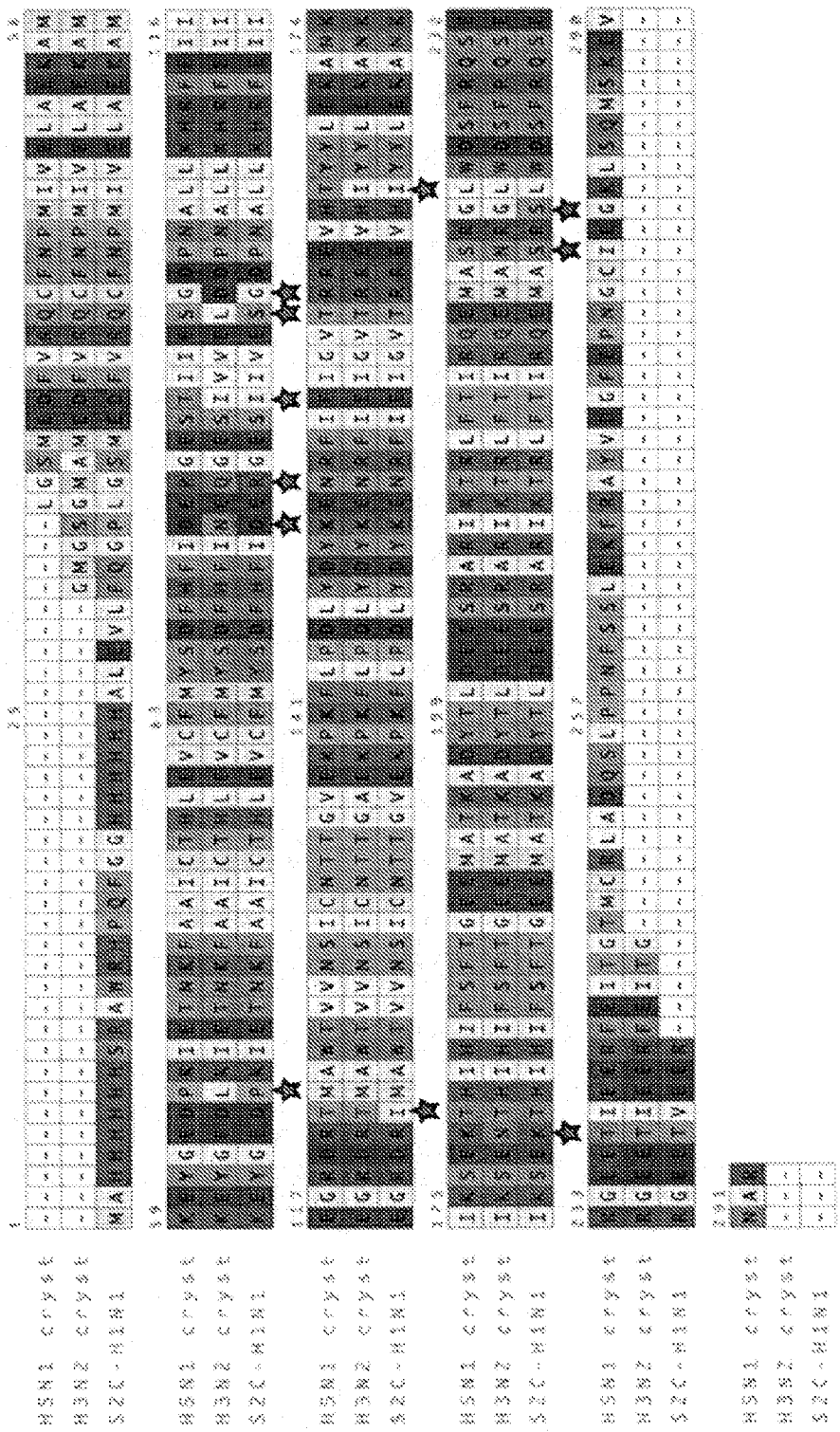
FIG. 7. Alignment of sequences for H5N1 (SEQ ID NO: 5) and H3N2 (SEQ ID NO: 6) crystallized flu endonuclease domains and the H1N1 construct designated S2C (SEQ ID NO: 1). Variable residues are marked with stars.

An alignment of the sequences for H5N1 (SEQ ID NO:5) and H3N2 (SEQ ID NO:6) crystallized flu endonuclease domains and the H1N1 construct designated S2C (SEQ ID NO:1) is shown in FIG. 7. The variable residues are marked with stars.

S2C (SEQ ID NO:1) was expressed in BL21 (RIL) cells (Stratagene). The BL21 cells were grown to an $OD_{600}$ of 0.8 and induced with 0.2 mM IPTG at 17 degrees Celsius for 17 hours. Cells were harvested by centrifugation and purified on Ni-NTA (Qiagen) according to manufacturers recommendations. The dual hexaHis tag (SEQ ID NO:4) was then removed by 3C protease cleavage. S2C (SEQ ID NO:2) was further purified by size exclusion chromatography using HiLoad 26/60 Superdex 75 (GE Healthcare). The buffer used for size exclusion and the final buffer for storage of the protein was 100 mM NaCl and 20 mM Tris pH 8.0. The protein was concentrated to 10 mg/ml using a Ultrafree 10K (Millipore), aliquoted and stored at −80 degrees Celsius.

For form 1 crystals, S2C (SEQ ID NO:2) was mixed in equal volumes with 1 mM manganese chloride, 200 mM MES pH 6.7, 25% PEG 8000, 100 mM ammonium sulfate, 10 mM magnesium acetate, 10 mM taurine, and 50 mM sodium fluoride. For form 2, crystallization was performed with equal volumes of S2C (SEQ ID NO:2) and Tris pH 8.5, 1.5 M ammonium sulfate, and 12% glycerol. For form 3 crystallization was performed the same as for form 1 but with the addition of a 6-mer RNA of the sequence GAAUCA. All crystallization was performed at 20 degrees Celsius.

B. Fragment Soaking, Data Collection, and Processing

Most soaks of fragments or other ligands were performed by taking crystals and by step-wise gradient shifting the surrounding crystallization solution to 1 mM manganese sulfate, 200 mM HEPES pH 7.7, 25% PEG 8 k, 50 mM ammonium sulfate, 5 mM magnesium acetate, and 10% ethylene glycol. 80-100 mM L-Arginine was included to improve solubility of the fragments. Crystals were then soaked with the ligand for 2 hours at 20 degrees Celsius before placing into liquid nitrogen for storage. X-ray diffraction data set collection was performed at the Cornell High Energy Synchrotron Source (CHESS) F1 beamline, and the National Synchrotron Light Source (NSLS) beamlines X25 and X29. The diffraction data were indexed, processed, scaled and merged using HKL2000 (Otwinowski et al., 1999). Initial datasets from crystals were collected to minimize the time of collection by increasing oscillation range per image and decreasing exposure time. $F_o$-$F_o$ maps were immediately calculated using CNS. Datasets from crystals containing bound fragments were then recollected to improve maximum X-ray diffraction resolution. High-resolution data sets containing bound fragments were further processed using CCP4 and CNS.

C. Endonuclease Activity Assay

The endonuclease assay used a single-stranded DNA probe with the sequence TGGCAATATCAGCTCCACA (SEQ ID NO:3) (Applied Biosystems). The 5' end of the probe (SEQ ID NO:3) contains the fluorophore 6-carboxyfluorescein (6-FAM) and the 3' ends contain minor groove binder non-fluorescent quencher (mgbnfq). The reaction buffer contains 50 mM Tris pH 7.5, 100 mM sodium chloride, 1 mM TCEP, 5 mM magnesium chloride, and 1 mM CHAPS. The compound, probe (SEQ ID NO:3), and S2C (SEQ ID NO:2) (250 nM) are preincubated in the reaction buffer for 30 minutes at room temperature before the reaction is enhanced with the addition of 0.2 mM manganese sulfate. Fluorescence is then measured in a Varioskan Fluorometer (Thermo Scientific) set to an excitation of 488 nm and emission of 518 nm. Fluorescence is measured at various time points and activity/inhibition is calculated using Excel.

REFERENCES

Bloom et al., Science. 2010; 328(5983):1272-5.
Congreve et al., J Med Chem. 2008; 51(13):3661-80.
Das et al., Nat Struct Mol Biol. 2010; 17(5):530-8.
Dias et al., Nature. 2009; 458(7240):914-8.
Hara et al., J Virol. 2006; 80(16):7789-98.
Klumpp et al., J Biol Chem. 2000; 275(9):6181-8.
Lamb R A, and Krug, R. M. Orthomyxoviridae: the viruses and their replication. In: Knipe D M, and Howley, P. M., editor. Fields Virology, 4th edition. Philadelphia: Lippincott Williams & Wilkins; 2001. p. 1487-532.
Memoli et al., J Infect Dis. 2011; 203(3):348-57.
Moscona, N Engl J Med. 2005; 353(25):2633-6.
Parkes et al., J Med Chem. 2003; 46(7):1153-64.
Rees et al., Nat Rev Drug Discov. 2004; 3(8):660-72.
Taubenberger et al., Nature. 2005; 437(7060):889-93.
Tomassini et al., Antimicrob Agents Chemother. 1994; 38(12):2827-37
Yuan et al., Nature. 2009; 458(7240):909-13.
Zhao et al., J Virol. 2009; 83(18):9024-30.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. An isolated or purified protein with an amino acid sequence at least 95% identical to SEQ ID NO: 1.

2. The amino acid sequence of claim 1, wherein the sequence is SEQ ID NO:1.

3. A crystal formed from an isolated or purified protein with an amino acid sequence consisting of SEQ ID NO:2, which is Form I, Form II or Form III, wherein Form I has space group $C222_1$ and unit cell parameters of a=86.66-90.86, b=100.83-102.94, and c=65.95-66.62 Å, and $\alpha=\beta=\gamma=90.0°$; wherein Form II has space group $P2_1$ and unit cell parameters of a=63.61-64.97, b=65.44-66.78, and c=64.22-65.95 Å, and $\alpha=\gamma=90.0°$, $\beta=112.66-114.73°$; and wherein Form III has space group C2 and unit cell parameters of a=102.51, b=89.25, and c=132.61 Å, and $\alpha=\gamma=90.0°$, and $\beta=89.98°$.

4. The crystal of claim 3, which is Form I.

5. The crystal of claim 3, which is Form II.

6. The crystal of claim 3, which is Form III.

7. The crystal of claim 4, in complex with a nucleoside monophosphate (NMP) or an endonuclease inhibitor.

8. A method, comprising contacting a compound with the crystal of claim 4 and determining the structure of the crystal in complex with the compound.

9. A crystal formed from an isolated or purified protein with an amino acid sequence consisting of SEQ ID NO:2, which is Form I, Form II or Form III, wherein Form I has space group $C222_1$ and unit cell parameters of a=88.28, b=102.06, and c=66.26 Å, and $\alpha=\beta=\gamma=90.0°$; wherein Form II has space group $P2_1$ and unit cell parameters of a=65.38, b=66.91, and c=66.14 Å, and $\alpha=\gamma=90.0°$, $\beta=115.34°$; wherein Form III has space group C2 and unit cell parameters of a=102.51, b=89.25, and c=132.61 Å, and $\alpha=\gamma=90.0°$, $\beta=89.98°$, and wherein the parameters can vary by +/−5%.

10. The crystal of claim 9, which is Form I.

11. The crystal of claim 9, which is Form II.

12. The crystal of claim 9, which is Form III.

13. The crystal of claim 10, in complex with a nucleoside monophosphate (NMP) or an endonuclease inhibitor.

14. A method, comprising contacting a compound with the crystal of claim 10 and determining the structure of the crystal in complex with the compound.

* * * * *

SEQUENCE LISTING

```
<160> NUMBER OF SEQ ID NOS: 6

<210> SEQ ID NO 1
<211> LENGTH: 241
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 1

Met Ala His His His His His Ser Arg Ala Trp Arg His Pro Gln
1               5                   10                  15

Phe Gly Gly His His His His His Ala Leu Glu Val Leu Phe Gln
                20                  25                  30

Gly Pro Leu Gly Ser Met Glu Asp Phe Val Arg Gln Cys Phe Asn Pro
            35                  40                  45

Met Ile Val Glu Leu Ala Glu Lys Ala Met Lys Glu Tyr Gly Glu Asp
        50                  55                  60

Pro Lys Ile Glu Thr Asn Lys Phe Ala Ala Ile Cys Thr His Leu Glu
65              70                  75                  80

Val Cys Phe Met Tyr Ser Asp Phe His Phe Ile Asp Glu Arg Gly Glu
                85                  90                  95

Ser Ile Ile Val Glu Ser Gly Asp Pro Asn Ala Leu Leu Lys His Arg
            100                 105                 110

Phe Glu Ile Ile Glu Gly Arg Asp Arg Ile Met Ala Trp Thr Val Val
        115                 120                 125

Asn Ser Ile Cys Asn Thr Thr Gly Val Glu Lys Pro Lys Phe Leu Pro
130                 135                 140

Asp Leu Tyr Asp Tyr Lys Glu Asn Arg Phe Ile Glu Ile Gly Val Thr
145                 150                 155                 160

Arg Arg Glu Val His Ile Tyr Tyr Leu Glu Lys Ala Asn Lys Ile Lys
                165                 170                 175

Ser Glu Lys Thr His Ile His Ile Phe Ser Phe Thr Gly Glu Glu Met
            180                 185                 190

Ala Thr Lys Ala Asp Tyr Thr Leu Asp Glu Glu Ser Arg Ala Arg Ile
        195                 200                 205

Lys Thr Arg Leu Phe Thr Ile Arg Gln Glu Met Ala Ser Arg Ser Leu
210                 215                 220

Trp Asp Ser Phe Arg Gln Ser Glu Arg Gly Glu Glu Thr Val Glu Glu
225                 230                 235                 240

Arg

<210> SEQ ID NO 2
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Pro Leu Gly Ser Met Glu Asp Phe Val Arg Gln Cys Phe Asn Pro
1               5                   10                  15

Met Ile Val Glu Leu Ala Glu Lys Ala Met Lys Glu Tyr Gly Glu Asp
                20                  25                  30

Pro Lys Ile Glu Thr Asn Lys Phe Ala Ala Ile Cys Thr His Leu Glu
            35                  40                  45

Val Cys Phe Met Tyr Ser Asp Phe His Phe Ile Asp Glu Arg Gly Glu
        50                  55                  60

Ser Ile Ile Val Glu Ser Gly Asp Pro Asn Ala Leu Leu Lys His Arg
65                  70                  75                  80

```
Phe Glu Ile Ile Glu Gly Arg Asp Arg Ile Met Ala Trp Thr Val Val
                85                  90                  95

Asn Ser Ile Cys Asn Thr Thr Gly Val Glu Lys Pro Lys Phe Leu Pro
            100                 105                 110

Asp Leu Tyr Asp Tyr Lys Glu Asn Arg Phe Ile Glu Ile Gly Val Thr
        115                 120                 125

Arg Arg Glu Val His Ile Tyr Tyr Leu Glu Lys Ala Asn Lys Ile Lys
    130                 135                 140

Ser Glu Lys Thr His Ile His Ile Phe Ser Phe Thr Gly Glu Glu Met
145                 150                 155                 160

Ala Thr Lys Ala Asp Tyr Thr Leu Asp Glu Glu Ser Arg Ala Arg Ile
                165                 170                 175

Lys Thr Arg Leu Phe Thr Ile Arg Gln Glu Met Ala Ser Arg Ser Leu
            180                 185                 190

Trp Asp Ser Phe Arg Gln Ser Glu Arg Gly Glu Glu Thr Val Glu Glu
        195                 200                 205

Arg

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tggcaatatc agctccaca                                                  19

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Gly Ser Met Glu Asp Phe Val Arg Gln Cys Phe Asn Pro Met Ile
1               5                   10                  15

Val Glu Leu Ala Glu Lys Ala Met Lys Glu Tyr Gly Glu Asp Pro Lys
                20                  25                  30

Ile Glu Thr Asn Lys Phe Ala Ala Ile Cys Thr His Leu Glu Val Cys
            35                  40                  45

Phe Met Tyr Ser Asp Phe His Phe Ile Asp Glu Arg Gly Glu Ser Thr
        50                  55                  60

Ile Ile Glu Ser Gly Asp Pro Asn Ala Leu Leu Lys His Arg Phe Glu
65                  70                  75                  80
```

```
Ile Ile Glu Gly Arg Asp Arg Thr Met Ala Trp Thr Val Val Asn Ser
                85                  90                  95

Ile Cys Asn Thr Thr Gly Val Glu Lys Pro Lys Phe Leu Pro Asp Leu
            100                 105                 110

Tyr Asp Tyr Lys Glu Asn Arg Phe Ile Glu Ile Gly Val Thr Arg Arg
        115                 120                 125

Glu Val His Thr Tyr Tyr Leu Glu Lys Ala Asn Lys Ile Lys Ser Glu
    130                 135                 140

Lys Thr His Ile His Ile Phe Ser Phe Thr Gly Glu Glu Met Ala Thr
145                 150                 155                 160

Lys Ala Asp Tyr Thr Leu Asp Glu Glu Ser Arg Ala Arg Ile Lys Thr
                165                 170                 175

Arg Leu Phe Thr Ile Arg Gln Glu Met Ala Ser Arg Gly Leu Trp Asp
            180                 185                 190

Ser Phe Arg Gln Ser Glu Arg Gly Glu Thr Ile Glu Glu Arg Phe
        195                 200                 205

Glu Ile Thr Gly Thr Met Cys Arg Leu Ala Asp Gln Ser Leu Pro Pro
    210                 215                 220

Asn Phe Ser Ser Leu Glu Lys Phe Arg Ala Tyr Val Asp Gly Phe Glu
225                 230                 235                 240

Pro Asn Gly Cys Ile Glu Gly Lys Leu Ser Gln Met Ser Lys Glu Val
                245                 250                 255

Asn Ala Arg

<210> SEQ ID NO 6
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Met Gly Ser Gly Met Ala Met Glu Asp Phe Val Arg Gln Cys Phe
1               5                   10                  15

Asn Pro Met Ile Val Glu Leu Ala Glu Lys Ala Met Lys Glu Tyr Gly
            20                  25                  30

Glu Asp Leu Lys Ile Glu Thr Asn Lys Phe Ala Ala Ile Cys Thr His
        35                  40                  45

Leu Glu Val Cys Phe Met Tyr Ser Asp Phe His Phe Ile Asn Glu Gln
    50                  55                  60

Gly Glu Ser Ile Val Val Glu Leu Asp Asp Pro Asn Ala Leu Leu Lys
65                  70                  75                  80

His Arg Phe Glu Ile Ile Glu Gly Arg Asp Arg Thr Met Ala Trp Thr
                85                  90                  95

Val Val Asn Ser Ile Cys Asn Thr Thr Gly Ala Glu Lys Pro Lys Phe
            100                 105                 110

Leu Pro Asp Leu Tyr Asp Tyr Lys Glu Asn Arg Phe Ile Glu Ile Gly
        115                 120                 125

Val Thr Arg Arg Glu Val His Ile Tyr Tyr Leu Glu Lys Ala Asn Lys
    130                 135                 140

Ile Lys Ser Glu Asn Thr His Ile His Ile Phe Ser Phe Thr Gly Glu
145                 150                 155                 160

Glu Met Ala Thr Lys Ala Asp Tyr Thr Leu Asp Glu Glu Ser Arg Ala
                165                 170                 175
```

-continued

```
Arg Ile Lys Thr Arg Leu Phe Thr Ile Arg Gln Glu Met Ala Asn Arg
            180                 185                 190

Gly Leu Trp Asp Ser Phe Arg Gln Ser Glu Arg Gly Glu Glu Thr Ile
            195                 200                 205

Glu Glu Arg Phe Glu Ile Thr Gly
            210                 215
```